(12) United States Patent
Eriksson

(10) Patent No.: US 8,256,046 B2
(45) Date of Patent: Sep. 4, 2012

(54) SANITARY PRODUCT

(75) Inventor: Goran Eriksson, Karlstad (SE)

(73) Assignee: Cellcomb Aktiebolag, Karlstad (SE)

( * ) Notice: Subject to any disclaimer, the term of this patent is extended or adjusted under 35 U.S.C. 154(b) by 725 days.

(21) Appl. No.: 11/574,195

(22) PCT Filed: Aug. 30, 2005

(86) PCT No.: PCT/SE2005/001249
§ 371 (c)(1),
(2), (4) Date: May 27, 2008

(87) PCT Pub. No.: WO2006/025781
PCT Pub. Date: Mar. 9, 2006

(65) Prior Publication Data
US 2010/0043146 A1    Feb. 25, 2010

(30) Foreign Application Priority Data

Sep. 3, 2004 (SE) .................... 0402127-7
Oct. 13, 2004 (SE) .................... 0402493-1

(51) Int. Cl.
*A47G 9/02* (2006.01)
(52) U.S. Cl. .................... 5/495; 5/500; 5/502
(58) Field of Classification Search .......... 5/495, 482, 5/490–491, 500–502
See application file for complete search history.

(56) References Cited

U.S. PATENT DOCUMENTS

| | | | |
|---|---|---|---|
| 5,851,937 A | 12/1998 | Wu et al. | |
| 6,017,601 A * | 1/2000 | Amsel | 428/36.1 |
| 2002/0148047 A1 | 10/2002 | Corzani | |
| 2003/0121101 A1 | 7/2003 | Corzani | |

FOREIGN PATENT DOCUMENTS

| | | |
|---|---|---|
| EP | 1 145 694 | 10/2001 |
| GB | 943979 | 12/1963 |
| GB | 2 384 702 | 8/2003 |
| JP | 10-066639 A | 3/1998 |
| JP | 2000-070097 A | 3/2000 |
| WO | WO 99/65370 A1 | 12/1999 |
| WO | 00/06372 | 2/2000 |
| WO | 01/92619 | * 12/2001 |

OTHER PUBLICATIONS

Supplementary European Search Report issued in PCT/SE2005/001249 dated Mar. 4, 2008, 6 pages.
Japanese Office Action with English translation corresponding to Japanese Application No. 2007-529772, dated Nov. 2, 2010.
Examination Report from UK-IPO issued in GB0706317.5, Oct. 1, 2008, 2 pages.
International Search Report for PCT/SE2005/001249 dated Nov. 8, 2005, 3 pages.

* cited by examiner

*Primary Examiner* — Fredrick Conley
(74) *Attorney, Agent, or Firm* — Pillsbury Winthrop Shaw Pittman, LLP

(57) ABSTRACT

The present invention relates to a sanitary product in the form of a disposable sheet or the like, consisting of a web-shaped material comprising a top comfort layer and a bottom barrier layer that are joined together by gluing or embossing without any intermediate layer, wherein the barrier layer is a breathable barrier layer, and said comfort layer is formed from a non-woven material, the basis weight of the comfort layer being equal to or greater than the basis weight of the barrier layer.

9 Claims, 2 Drawing Sheets

Fig. 4
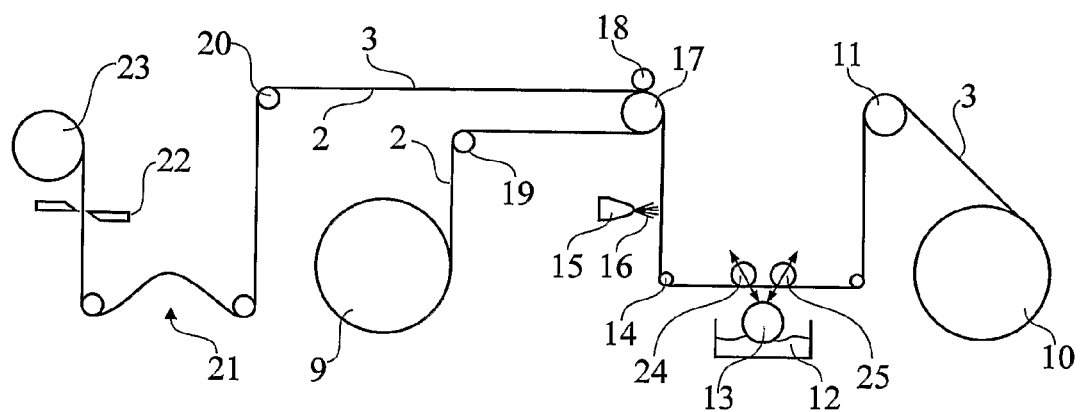
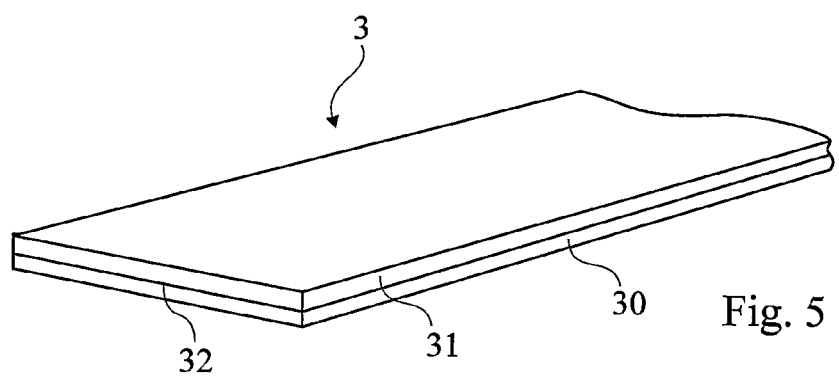
Fig. 5

SANITARY PRODUCT

CROSS REFERENCE TO RELATED APPLICATIONS

This is the U.S. National Phase of PCT/SE2005/001249, filed Aug. 30, 2005, which in turn claims priority to Swedish application Nos. 0402126-7, filed Sep. 3, 2004 and 0402493-1, Filed Oct. 13, 2004, all of which are incorporated herein in their entirety by reference.

TECHNICAL FIELD

A sanitary product, consisting of a web-shaped material comprising a top comfort layer and a bottom barrier layer, for disposable use in the form of sheets e.g. The invention also relates to a method of producing a disposable sanitary product comprising a web-shaped large area material intended to protect and/or provide comfort, preferably in the form of sheets, duvet covers or pillow cases, comprising the joining by a seam of two web-shaped parts.

PRIOR ART

It is known that there are many advantages in using disposable materials for certain sanitary products, such as sheets or the like, not at least within medical services in connection with geriatric care. Disposable sheets and similar products of today have the problem however that they allow various body fluids, such as blood, urine etc., to penetrate through the disposable product, and thereby to penetrate into bedclothes, mattresses, pillows and quilts. It is realised that this is non-beneficial from an economical as well as a sanitary point of view. Efforts have been made to laminate disposable products with different types of barrier layers, in order to prevent liquid from penetrating the disposable product, but no product has been made hitherto which has been accepted on the market, for comfort reasons.

A related, secondary problem is waste handling of such disposable products. Due to their nature and field of application, they can in principle not be reused, but must be destroyed. Today, this takes place in principle by incineration only. From an environmental point of view, incineration is not always a desirable form of destruction. Furthermore, the handling by incineration forms a logistical problem in terms of storage problems and transporting problems.

The products that create a considerable logistical problem are those that result in a large amount of waste, i.e. products creating a large waste volume. Typical products of that type are disposable sheets, pillow cases and duvet covers. Today, non-renewable raw materials, such as polypropylene, are almost exclusively used therefore. It is for certain known also to use renewable raw materials, such as cellulose fibres, as materials for such products, but as is described above, the recovery is associated with complications; especially as such products most often comprise some type of barrier layer that largely prevents recycling. Such disposable products are most often made from a web-shaped material that is sewn together to a desired shape and size.

BRIEF ACCOUNT OF THE INVENTION

It is an object of the present invention to minimise the above mentioned problems, which is achieved by a sanitary product in the form of a disposable sheet and similar, consisting of a web-shaped material comprising a top comfort layer and a bottom barrier layer that are joined together by gluing or embossing without any intermediate layer, wherein the barrier layer is a breathable barrier layer, and said comfort layer is formed from a non-woven material, the basis weight of the comfort layer being equal to or greater than the basis weight of the barrier layer.

Thanks to the solution according to the invention, a disposable sanitary product has been achieved, for sheets e.g., that provides a protection against liquid penetration and that also fulfils essential comfort requirements, and allows for a cost efficient production. Somewhat surprising, it has been shown that the combination according to the invention is experienced to be extra comfortable since it, in relation to known disposable products, is experienced as being considerably less rustling and considerably more pliable/flexible.

According to further aspects of the invention:
- said barrier function is achieved by a biodegradable material of renewable raw materials, preferably in the form of a breathable barrier layer, more preferably essentially comprising a starch-based material, it being preferable that a major part of the material of the disposable product is biodegradable, which results in the advantage that logistic problems of today can be essentially minimized, concerning sanitary products.
- the two layers are laminated by a glue, giving the advantage that a particularly cost efficient manufacturing can be obtained, while at the same time achieving good quality aspects.
- said glue is applied on less than 80% of the surface, preferably less than 40% of the surface, and even more preferred less than 20% of the surface, giving the advantage that a beneficial breathability can be maintained over the layers.
- the basis weight of each layer is 5-200 g/m$^2$, preferably 10-100 g/m$^2$, more preferred less than 50 g/m$^2$.
- the disposable product comprises two web-shaped parts that are held together by seams at at least two edge sections, preferably continuous seams made by an adhesive, which adhesive preferably contains biodegradable components in the main, giving the advantage that a cost efficient production can be achieved for disposable products containing large, web-shaped parts.
- at least one of the side edges consists of a folding of the web-shaped material, resulting in a particularly cost efficient production for certain applications.
- at least one of said edge sections is arranged to form an opening, with the purpose of being able to insert a desired item between said two parts.

The invention also relates to an advantageous method of producing a disposable sanitary product, resulting in the advantage that a very rational and cost efficient production can be achieved for many types of disposable products.

BRIEF DESCRIPTION OF THE DRAWINGS

In the following, the invention will be described in greater detail with reference to the attached drawing figures, of which:

FIG. 4 shows the principles of a set of machineries for production of a disposable product according to the invention, and FIG. 5 shows a web-shaped material that is preferred according to some embodiments and adapted to be used in connection with the invention.

DETAILED DESCRIPTION

Figure 1:
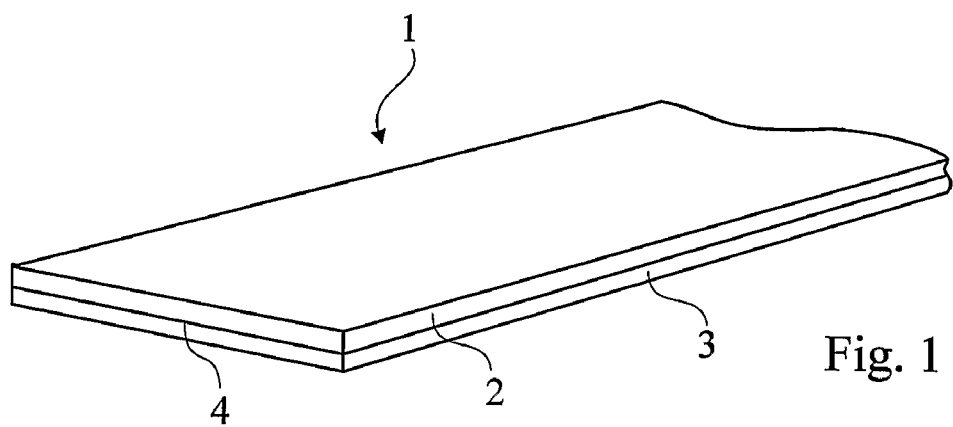
FIG. 1 schematically shows a sanitary product formed according to the invention.

FIG. 1 schematically shows a portion of a sanitary product 1, in the form of a disposable sheet 1, e.g. The sheet 1 is a laminate that comprises a comfort layer 2 and a barrier layer 3, which have been laminated by a cold-water glue. According to a preferred embodiment, the comfort layer 2 consists of a spunbonded non-woven material having a basis weight of about 20 g/m$^2$. The barrier layer 3 consists of a breathable polyethylene material having a basis weight of 20 g/m$^2$. The barrier layer is waterproof, but has a water vapour permeability of between 25 and 10000 g/24 h/30° C., preferably 600-9000 g/24 h/30° C.

According to another embodiment, the comfort layer 2 consists of a spunlaced non-woven material having a basis weight of about 45 g/m$^2$. Here too, the barrier layer 3 consists of a micro-porous, breathable polyethylene material having a basis weight of 20 g/m$^2$.

According to another embodiment, the comfort layer 2 consists of a spunlaced non-woven material having a basis weight of about 45 g/m$^2$, but having a barrier layer 3 consisting of a breathable starch material having a basis weight of about 16 g/m$^2$.

Figure 2:
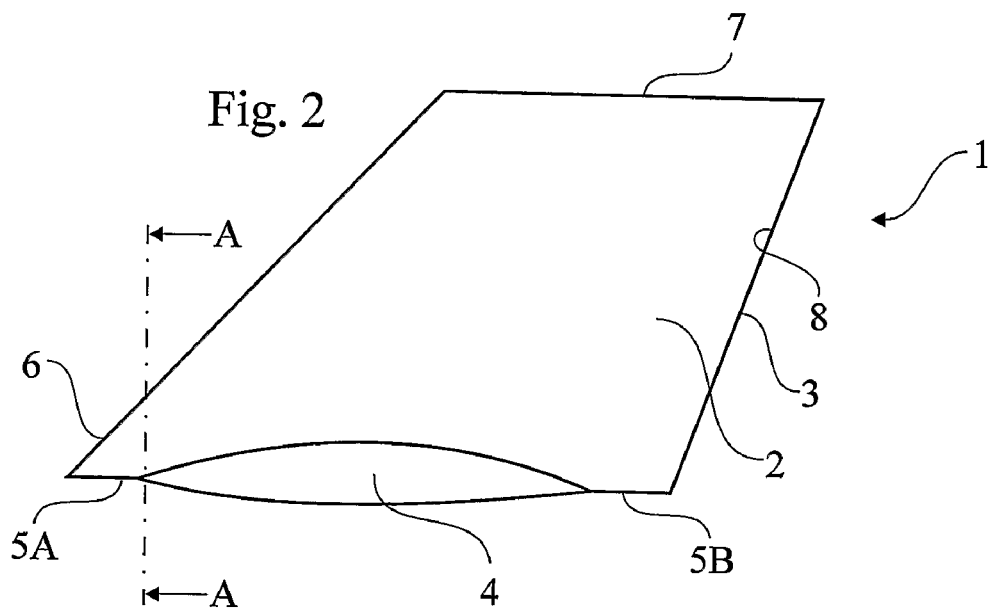
FIG. 2 shows a preferred disposable product according to the invention, in the form of a duvet cover, as seen in perspective from above.

FIG. 2 shows a duvet cover 1, formed according to the invention. It consists of an upper, web-shaped part 2, and a lower web-shaped part 3, having glued seams 5, 6, 7, 8 at their edge portions. At the rear edge 5, only a part, 5A and 5B, respectively, of the length is glued together, such that an opening 4 is formed between these limited seams 5A, 5B. The opening is intended for insertion of a quilt, as is known per se.

Figure 3:
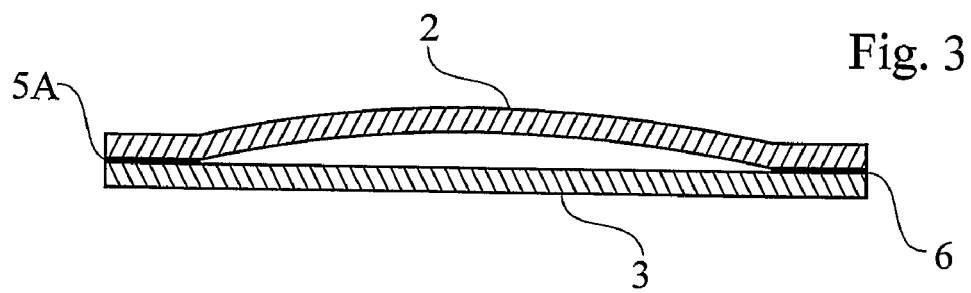
FIG. 3 shows a cross-section A-A through a duvet cover according to FIG. 2.

It is shown in detail in FIG. 3 that the web-shaped parts 2, 3 have been joined by strings of glue 5A and 6, respectively, having a width of about 10 mm, normally within the range of 5-20 mm. Preferably, the glue is formed from biodegradable components, but this is not decisive because the glue constitutes such a limited part of the total material included in a disposable product such as a duvet cover, and a small amount of non-biodegradable material can be allowed to be included in recycling. The web-shaped material 2, 3 also consist of biodegradable material, preferably in the form of a renewable fibrous raw material. It is also conceivable however, that a small portion of a non-renewable raw material is included in the structure of the web-shaped material, however at such an amount that it does not negatively affect recycling. The material used in the web-shaped material 2, 3 can for example be tissue, non-woven material, other types of web-shaped fibrous materials, and of course also various types of laminate.

FIG. 4 shows the principles of a set of machinery, according to a preferred embodiment, for production of a disposable product according to the invention. Two rolls 9, 10 are shown, containing a web-shaped and biodegradable raw material, preferably consisting completely of a renewable raw material such as cellulose fibres in the form of tissue. A first web-shaped material 2 is rolled off from a first roll 9, and a second web-shaped material 3 is rolled off from a second roll 10. Suitable guide rolls 11, 19 are arranged in connection with the rolling off, at both rolls 9, 10. The second web-shaped material 3 passes first through a lateral gluing station 12, 13, 24, 25, in which lateral seams of glue 5A, 5B and 7 are formed by a so called engraving roller 13 that intermittently contacts the web-shaped material 3 in order to apply glue along a desired extension. As is shown in the figure, two movable rollers 24, 25 are arranged above the engraving roller 13, one of these rollers 24 being an elongated unit, such that a continuous string of glue 7 is achieved as it moves downwards and presses the web-shaped material 3 against the engraving roller. The contact time is of very short duration, by the roller 24 conducting a fast movement down-and-up, such that a string of glue is applied that is between 1 and 10 cm, preferably 2-6 cm.

A pair of rollers 24 (only one being shown in the figure, due to the side view) are arranged to achieve the split lateral seam 5A, 5B, which rollers have a limited length corresponding to the length of the respective string of glue 5A and 5B, and at lateral positions that correspond to the positions of the respective string of glue 5A and 5B on the web-shaped material 3. When these rollers move downwards, limited strings of glue 5A, 5B will accordingly be applied to the web-shaped material 3.

As is realised, the rollers 24, 25 move alternatingly, such that every other lateral seam 7 will be continuous and every other will be split 5A, 5B.

After the lateral gluing, the web-shaped material 3 passes a pair of devices 15 (only one of which being shown in the figure, due to the side view), that applies the longitudinal seams 6, 8 by a spray 16. These devices 15, that are provided at both edges of the web-shaped material 3, will operate continuously, such that the strings of glue 6, 8 extend uninterrupted along each edge section.

After the longitudinally gluing application station 15, 16, the second web-shaped material 3 gets in contact with the first web-shaped material 2, at a pressing station comprising two contra-rotating rollers 17, 18, forming a nip. In this nip, the two web-shaped parts 2, 3 will be pressed together, whereby the strings of glue 5A, 5B, 6, 7, 8 will join together the two web-shaped materials. After additional guiding, the glued web-shaped material 2, 3 will arrive at a folding station 21, in which the web-shaped material is continuously folded together, such that its total width is considerably reduced. Such a folding station can e.g. allow for a reduction to a third or a sixth of the original width. Thereafter, the web-shaped material is cut by aid of a cutting device 22 that accordingly will cut in the middle of the applied string of glue 5A, 5B and 7, respectively, such that ready-cut products according to the invention are rolled up on a subsequent take-up roller.

FIG. 5 schematically shows a portion of a web-shaped material 3 that favourably can be used in some embodiments to make products according to the invention. The web-shaped material 3 is a laminate that comprises a comfort layer 31 and a barrier layer 30, which suitably have been laminated by a cold-water glue. According to a preferred embodiment, the comfort layer 31 consists of a spunbonded non-woven material having a basis weight of about 20 g/m$^2$. The barrier layer 30 consists of a breathable, starch-based material having a basis weight of about 20 g/m$^2$. The barrier layer is waterproof, but has a water vapour permeability of between 25 and 10000 g/24 h/30° C., preferably 600-9000 g/24 h/30° C. According to another embodiment, the comfort layer consists of a spunlaced non-woven material containing a renewable raw material and having a basis weight of about 45 g/m$^2$, and a barrier layer 30 consisting of a breathable starch material having a basis weight of about 16 g/m$^2$.

The invention is not limited to that described above, but may be varied within the scope of the claims. It is realised e.g., that instead of lamination by cold-water glue, the layers can be otherwise joined together, such as by embossing and/or hot glue. It is realised e.g. that many variations exist for choice of the biodegradable material, e.g. such that a certain amount is a biodegradable polymer material, of the PLA plastics type, e.g. a polymer material derived from sugar-beets or other suitable crops. It is also realised that if a barrier layer is to be used, it need not in some applications be breathable, even though this is preferable. It is also realised that the concept of a barrier function does not limit the invention to the arrangement of a dedicated barrier layer, but that it also comprises a barrier function that is integrated in a web-shaped material that also fulfils certain comfort requirements. Furthermore, it is realised that in some applications, only the upper, lateral string of glue 7 is needed, in case an opening 4 can be accepted that extends over the entire sheet, cover or pillow case. Moreover, it is realised that one (lateral or longitudinal) edge of such a product can be held together by folding a continuous, web-shaped material and thereafter conducting the gluing operation(s) on one or more of the remaining edges, which as such will make the arrangement of a continuously operating production machinery more difficult/expensive, but which also results in the advantage that the lateral gluing possibly can be completely eliminated (being completely open in one lateral end). The skilled person will furthermore realise that some of the described features according to the invention can be used also in connection with non-biodegradable materials, for example with the object of facilitating the production of such disposable products. The skilled man will also realise that the term "biodegradable material" is not limited to a renewable raw material, which however is preferred from an environmental point of view.

It is furthermore realised that many modifications can be made concerning the exemplified production equipment, still being within the scope of the method according to the invention. It is realised e.g., that instead of having a limited application of glue (at certain edge sections), a desired opening, or desired openings, can be achieved by punching/cutting the adhesive seam away, whereby an opening is achieved. For example, in the duvet cover shown in FIG. 1, openings can beneficially be formed also at opposing edge portions, by cutting the respective corner area, such that openings are formed for insertion of hands in connection with the insertion of a quilt inside the duvet cover. Thus, it is realised that in such a modification, only one roller 24 is required to achieve the lateral gluing, i.e. an elongated roller that applies glue over the entire length of the web, at every lateral seam. It is also realised that instead of cutting the material loose, partial or complete perforations can be used, whereby the disposable product is supplied to the user on a roll, to be released from the roll by the user by tearing the perforation.

Another modification that lies within the scope of the invention is to apply two adjacent, lateral seams on either side of the position at which a cutting/perforation of a short side of the web-shaped material is intended to be applied. This type of modification is an advantage in connection with the production, by allowing for a "margin of error" for the positioning of the cut/perforation, which might be desirable in some situations. The reason for this is that the web-shaped material normally should be run through the set of machinery at a certain tensile stress, and given that the web-shaped material has a certain elasticity, this results in combination in that it can be complicated to predict precisely where the intended cut/perforation will end up in relation to the lateral glues. By then applying two lateral glues at a spacing of about 3-10 cm, a "margin of error" is achieved that allows for a certain deviation in the cut/perforation in relation to the ideal positioning of the cut/perforation. Given that the projecting, cut portion of the duvet cover will be turned towards the inside, it is realised that such "overhang" need not be a disadvantage from the user's point of view. From a material utilisation point of view, it is however beneficial to use a method as described in connection with FIG. 3, which may however require use of a guiding/sensing arrangement in order to achieve a desired precision in the positioning of the cut/perforation. In this connection, it is realised that such guiding/sensing arrangements beneficially can be used in case it is desired instead of cutting small openings for the hands, to achieve such by coating discontinuously along the side edges, i.e. instead to create such openings by eliminating the application of glue at pre-defined positions, such that the openings are created directly in the process, due to the absence of glue at the desired positions.

Finally, it is realised that the biodegradable laminate described in connection with FIGS. 2, 3 and 5, need not be limited by the features of claim 1, but that the novel aspects concerning biodegradability given for this embodiment, can be made subject of a protection of its own, in a divisional patent application.

The invention claimed is:

1. A sanitary product in the form of a disposable sheet, comprising:
    a web-shaped material comprised substantially of biodegradable material, the web-shaped material including a top comfort layer and a bottom barrier layer without any intermediate layer interposed therein;
    wherein, the barrier layer is a breathable barrier layer,
    wherein, the comfort layer is formed from a non-woven material and the basis weight of the comfort layer is configured to be equal to or greater than the basis weight of the barrier layer, and
    wherein, the top comfort layer and bottom barrier layer are affixed together for less than 80% of the surface by an adhesive seam containing mainly biodegradable components, the adhesive seam disposed on at least two edge portions along a periphery of the top comfort and bottom barrier layers while an additional edge portion is arranged to remain unattached to define an opening in the disposable sheet.

2. The sanitary product according to claim 1, the barrier function is achieved by a biodegradable material from renewable raw materials in the form of a breathable barrier layer.

3. The sanitary product according to claim 2, wherein the breathable barrier layer essentially comprises a starch-based material.

4. The sanitary product according to claim 1, wherein the top comfort layer and the bottom barrier layer are laminated by a glue.

5. The sanitary product according to claim 4, wherein the glue is applied on less than 80% of the surface.

6. The sanitary product according to claim 5, wherein the glue is applied on less than 40% of the surface.

7. The sanitary product according to claim 1 in that a major part of the material comprised in the disposable product, is biodegradable.

8. The sanitary product according to any one of the preceding claims, wherein the basis weight of each layer is 5-200 $g/m^2$.

9. The sanitary product according to claim 8 wherein the basis weight of each layer is about 10-100 $g/m^2$.

* * * * *